United States Patent [19]

Ryschka et al.

[11] Patent Number: 4,611,590
[45] Date of Patent: Sep. 16, 1986

[54] ARRANGEMENT FOR ADDING LIQUID ANESTHETIC TO THE RESPIRATORY GAS SUPPLIED TO A PATIENT

[75] Inventors: Martin Ryschka, Stockelsdorf; Wolfgang Falb, Krumesse; Peter Büttner, Stockelsdorf; Carl-Friedrich Wallroth, Lübeck, all of Fed. Rep. of Germany

[73] Assignee: Drägerwerk Aktiengesellschaft, Lübeck, Fed. Rep. of Germany

[21] Appl. No.: 675,734

[22] Filed: Nov. 28, 1984

[30] Foreign Application Priority Data

Jan. 20, 1984 [DE] Fed. Rep. of Germany ....... 3401923

[51] Int. Cl.$^4$ ............................................. A61M 16/00
[52] U.S. Cl. ............................ 128/203.14; 128/204.21
[58] Field of Search ...................... 128/202.22, 203.12, 128/203.14, 203.22, 203.25–203.27, 204.17, 204.19, 204.21–204.22, 204.29

[56] References Cited

U.S. PATENT DOCUMENTS

| 3,651,805 | 3/1972 | Breiling | 128/203.14 X |
| 4,477,395 | 10/1984 | Albando | 128/203.14 X |

FOREIGN PATENT DOCUMENTS

| 2346730 | 4/1975 | Fed. Rep. of Germany | 128/203.12 |
| 3234474 | 3/1984 | Fed. Rep. of Germany | 128/203.12 |

OTHER PUBLICATIONS

Olsson, S. et al, "Respirator Intended for Connection to Human or Animal Airways", PCT Intnl. Publ. No. WO 82/0314, publ. Sep. 16, 1982.

Primary Examiner—Kyle L. Howell
Assistant Examiner—Francis J. Jaworski
Attorney, Agent, or Firm—Walter Ottesen

[57] ABSTRACT

The invention is directed to an arrangement for adding liquid anesthetic medium to the respiratory gas to be directed to a patient and is applicable to a closed respiratory system wherein an adequate quantity of the anesthetic medium must be supplied in a small respiratory gas volume and is also applicable to an open system wherein large quantities of anesthetic medium are required. The arrangement of the invention includes a plurality of tanks containing anesthetic mediums and a selection switch which can be selectively switched to any one of the tanks. A pump is located after the selection switch and a change-over switch permits switching the anesthetic medium from the pump to an anesthetic medium vaporizer and a swirl chamber. The anesthetic medium is vaporized in the vaporizer and then conducted at high concentration into the respiratory gas directed to the patient. The gas can be guided in a closed system. In the swirl chamber, the anesthetic medium is vaporized into the fresh gas flow which then is conducted to the patient in the form of respiratory gas. A control arrangement monitors and, with data from corresponding measuring devices, controls the preselected sequences.

5 Claims, 4 Drawing Figures

ARRANGEMENT FOR ADDING LIQUID ANESTHETIC TO THE RESPIRATORY GAS SUPPLIED TO A PATIENT

FIELD OF THE INVENTION

The invention relates to an arrangement for adding liquid anesthetic to the respiratory gas to be supplied to a patient and includes equipment for supplying the respiratory gas and the anesthetic.

BACKGROUND OF THE INVENTION

The apparatus of anesthetic technology should provide the possibility of permitting different anesthetic mediums to be utilized as required by means of change-over switching. It should be possible to introduce the anesthetic mediums with the same precision either into the fresh gas flow or directly into the patient system.

Published German patent application DE-OS No. 31 16 951 discloses an arrangement for adding liquid anesthetic medium into the respiratory gas to be supplied to a patient and contains a heatable swirl chamber into which the anesthetic medium is fed with the aid of a pump from the tank holding the anesthetic medium. The anesthetic medium enters the swirl chamber tangentially with the stream of respiratory gas where it develops into a cyclone-like flow and is vaporized. A heater of the swirl chamber is controlled with the aid of a temperature sensor and provides the heat needed for vaporization. The respiratory gas flows out again through an outlet whereat its temperature is checked. The respiratory gas now enriched with the anesthetic medium is then supplied to the patient. A control and evaluation circuit connected to sensors conducts the measurements and releases an alarm or controls when deviations from desired values was detected.

SUMMARY OF THE INVENTION

It is an object of the invention to provide an arrangement for adding liquid anesthetic medium into the respiratory gas supplied to a patient and wherein various anesthetic mediums are available by means of selective switching.

It is further object of the invention to provide such an arrangement wherein the anesthetic mediums are conducted either into the fresh gas or, after vaporization by heating, directly into the patient system and wherein the arrangement is easily monitored by the operator thereof and is simple to switch.

The advantages achieved by the invention are especially to be seen, on the one hand, in its application to a closed respiratory system wherein the anesthetic medium vaporizer is required to bring adequate quantities of anesthetic medium into the respiratory gas system; and, on the other hand, in its application to an open respiratory system wherein large quantities of anesthetic medium are required which must be provided evenly via a buffer volume, the foregoing being achieved with aid of the swirl chamber.

BRIEF DESCRIPTION OF THE DRAWING

The invention will now be described with reference to the drawing wherein.

DESCRIPTION OF THE PREFERRED EMBODIMENTS OF THE INVENTION

Figure 1:
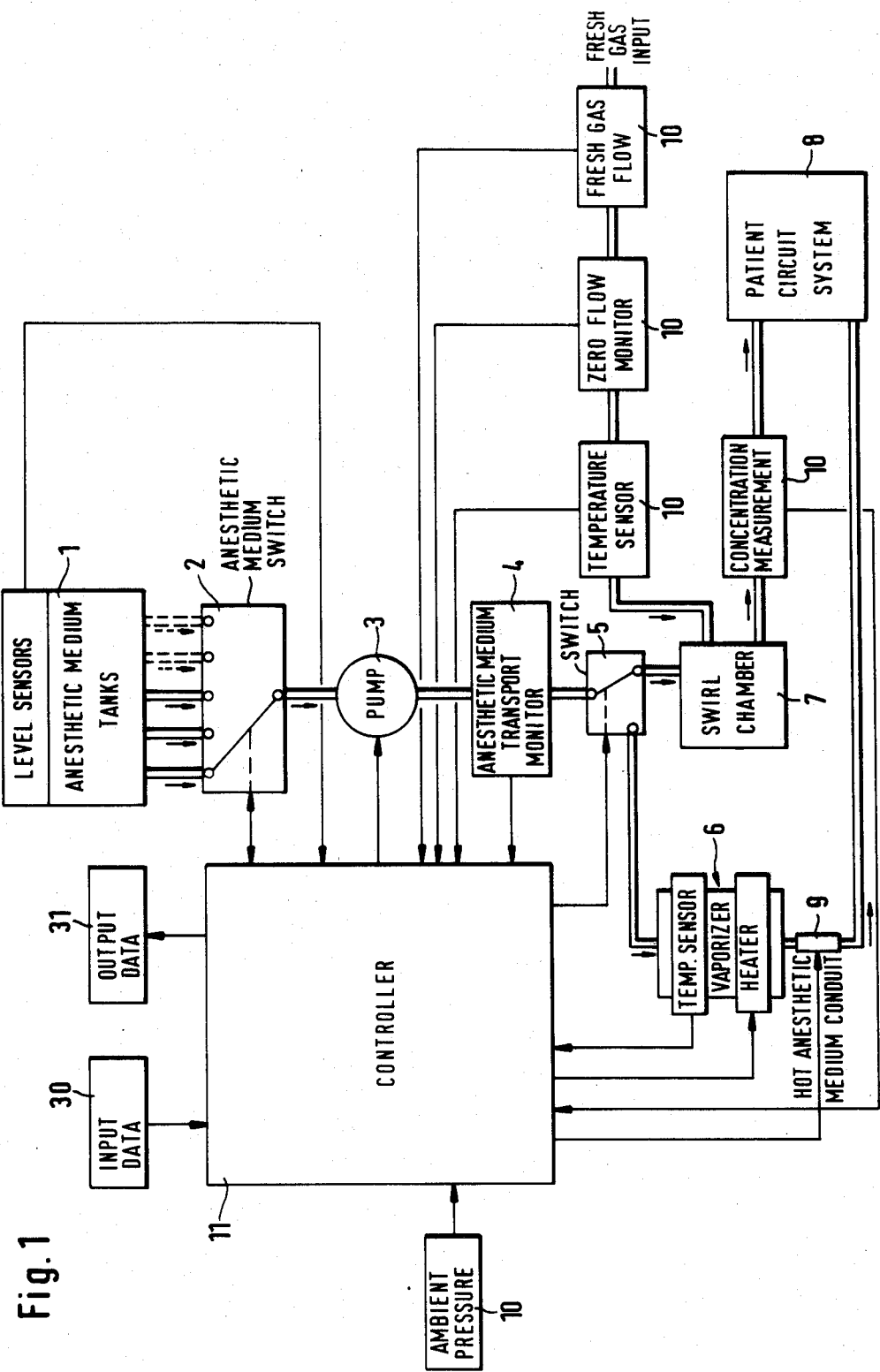
FIG. 1 is a block diagram of the arrangement according to the invention for adding liquid anesthetic medium into the respiratory gas supplied to a patient.

The arrangement for adding liquid anesthetic mediums to the respiratory gas to be supplied to a patient includes the following components which are described below in accordance with the sequence of the flow through the arrangement.

Reference numeral 1 identifies one or more tanks for holding the anesthetic mediums and the necessary fill level indicators and metering devices associated therewith. Reference numeral 2 identifies an anesthetic medium selective switch device for selectively switching to various anesthetic mediums. The arrangement further includes a pump 3 and an anesthetic medium transport monitor 4 as well as a change-over switch 5 for selectively switching the flow of the anesthetic mediums to an anesthetic medium vaporizer 6 and a swirl chamber 7. The transport monitor 4 discerns between a flow and no-flow condition and gives this information to the controller 11.

The vaporized or evaporated anesthetic medium is conducted from the vaporizer 6 or swirl chamber 7 into the respiratory gas system 8 (the patient system or the fresh gas) to the patient. A conduit 9 equipped with a heater connects the anesthetic medium vaporizer 6 to the respiratory gas system 8. Measuring devices 10 monitor the data and direct the same to a controller 11 which evaluates the data to control the components of the arrangement.

Referring to FIG. 1, reference numerals 30 and 31 identify peripheral devices and are represented by boxes having the legends "Input Data" and "Output Data", respectively. The input data is provided by the user and can be dosage, anesthetic medium, flow rate and other treatment parameters. On the other hand, the output data is data given by the controller 11 according to the information of the respective monitors and measuring devices.

Figure 2:
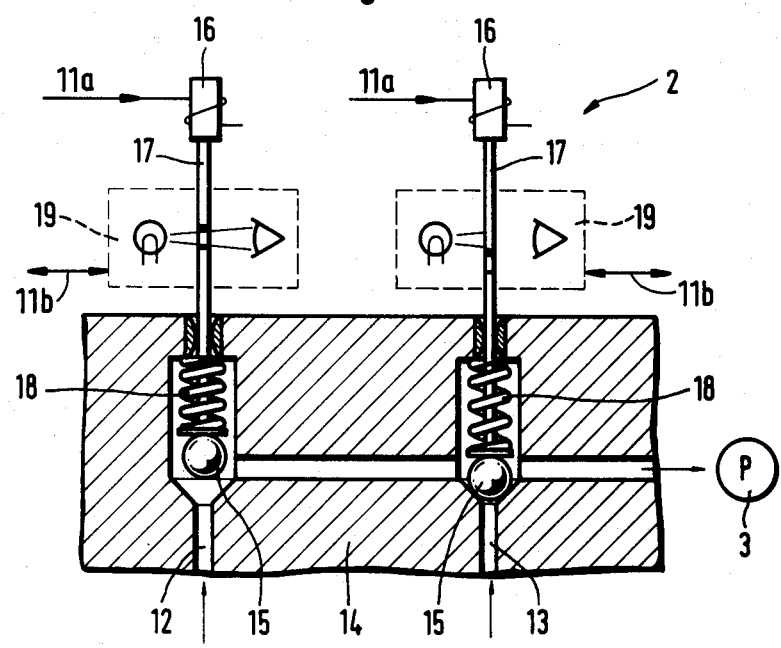
FIG. 2 is a schematic of the selective switch for selectively switching to a desired anesthetic medium; and, FIG. 3 is a side elevation schematic representation, partially in section, of a monitoring arrangement of the pump motor; and, FIG. 4 is a front elevation view of the disc and induction coils of the monitoring arrangement of FIG. 3.
Figure 3:
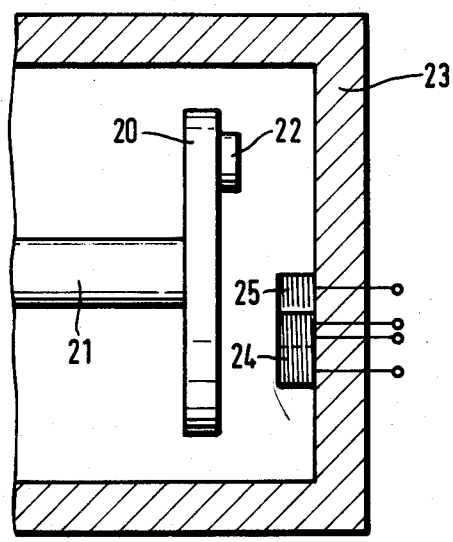
Figure 4:
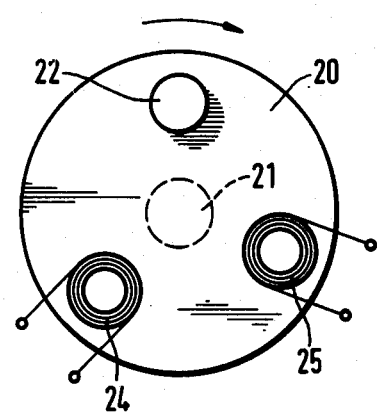

Referring now to FIG. 2, conduits 12 and 13 connect corresponding ones of the anesthetic medium tanks 1 to the anesthetic medium selective switch device 2. The conduits 12 and 13 terminate at corresponding ones of ball valves 15 arranged in a housing 14. The ball valves 15 are opened by lifting rods 17 with the aid of electromagnets 16 which are connected to controller 11 via control leads 11a. The ball valves 15 are spring-biased by coil spring 18 so as to cause them to close when the rods 17 are released. Photoelectric light barriers 19 on the rods 17 are connected to the controller 11 via leads 11b and indicate the switching position and control the ball valves 15.

The motor of pump 3 is monitored by means of a disc 20 fixedly mounted on the rotor shaft 21 of the motor of the piston pump and which carries permanent magnet 22. The permanent magnet 22 is directed past induction coils 24, 25 mounted on the motor housing 23 in spaced relationship from each other. The induced pulses provide information as to whether the rotor rotates properly and with what rotational velocity it rotates. If the pulses fall outside of a predetermined time window, a warning is generated and the pump is switched off.

It is understood that the foregoing description is that of the preferred embodiments of the invention and that various changes and modifications may be made thereto without departing from the spirit and scope of the invention as defined in the appended claims.

What is claimed is:

1. Apparatus for adding liquid anesthetic medium into the respiratory gas supplied to a patient, the arrangement comprising:
   a plurality of tanks containing anesthetic mediums;
   pump means for pumping the anesthetic medium of said tanks;
   selective switching means for selectively switching said pump means to any one of said plurality of tanks;
   vaporizer means for vaporizing the anesthetic medium and supplying the same at pure concentration for the respiratory gas to the patient;
   swirl chamber means adapted for connection to a supply of fresh gas and for vaporizing the anesthetic medium into the flow of fresh gas and conducting the same for respiratory gas to the patient;
   change-over switching means selectively switchable between a first position for conducting the anesthetic medium from said pump means only to said vaporizer means and a second position for conducting the anesthetic medium from said pump means only to said swirl chamber component means;
   monitoring means for monitoring data from said tanks and at least one of said pump means, said selective switching means, and said vaporizer means; and,
   control means for receiving and evaluating said data and for controlling at least one of said means in response to the evaluated data.

2. The apparatus of claim 1, said selective switching component means comprising:
   a plurality of ball valve means corresponding to respective ones of said tanks;
   each of said ball valve means being movable between a closed position whereat the flow of anesthetic medium to said pump component means is blocked and an open position whereat the anesthetic medium flows freely to said pump component means from the tank corresponding to the valve means;
   a plurality of movable rods operatively connected to corresponding ones of said valve means;
   electromagnetic means for actuating said rods to operate corresponding ones of said valve means; and,
   light barrier means corresponding to respective ones of said rods for monitoring the closed and open positions thereof.

3. The apparatus of claim 2, said pump means comprising:
   a pump for pumping the anesthetic medium;
   a motor having a shaft and being operatively connected to said pump for driving the same;
   monitoring means for monitoring the operation of said motor, said monitoring means including:
   a disc mounted on said shaft;
   a permanent magnet mounted on said disc; and,
   two induction coils mounted adjacent the path of said magnet on said disc thereby causing said coils to generate pulses indicative of the operation of said motor.

4. The apparatus of claim 3, said vaporizer means comprising: a vaporizer; a conduit extending from said vaporizer for supplying the vaporized anesthetic medium for the respiratory gas system; and, heater means arranged at said conduit for heating the vaporized anesthetic medium as it flows therethrough.

5. Apparatus for adding liquid anesthetic medium into the respiratory gas supplied to a patient, the arrangement comprising:
   a tank containing an anesthetic medium;
   pump means for pumping the anesthetic medium of said tank;
   vaporizer means receiving said anesthetic medium for vaporizing said medium and supplying the same at pure concentration for the respiratory gas to the patient;
   swirl chamber means adapted for connection to a supply of fresh gas and for vaporizing the anesthetic medium into the flow of fresh gas and conducting the same for respiratory gas to the patient;
   change-over switching means selectively switchable between a first position for conducting the anesthetic medium from said pump means only to said vaporizer means and a second position for conducting the anesthetic medium from said pump means only to said swirl chamber means;
   monitoring means for monitoring data from said tank and at least one of said pump means, and said vaporizer means; and,
   control means for receiving and evaluating said data and for controlling at least one of said means in response to the evaluated data.

* * * * *